United States Patent
Hois et al.

(10) Patent No.: US 6,265,589 B1
(45) Date of Patent: Jul. 24, 2001

(54) MIXTURES OF ALKYLATED METHYLOLATED 4,5-DIHYDROXY-IMIDAZOLIDIN-2-ONES

(75) Inventors: Pia Hois, Birkenau; Ferdinand Lippert, Bad Dürkheim; Jürgen Reichert, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/331,583

(22) PCT Filed: Dec. 30, 1997

(86) PCT No.: PCT/EP97/07318

§ 371 Date: Jun. 30, 1999

§ 102(e) Date: Jun. 30, 1999

(87) PCT Pub. No.: WO98/29393

PCT Pub. Date: Jul. 9, 1998

(30) Foreign Application Priority Data

Dec. 30, 1996 (DE) .............................. 196 54 739

(51) Int. Cl.[7] ................................. C07D 233/40
(52) U.S. Cl. ........................................... 548/317.5
(58) Field of Search ........................... 548/317.5

(56) References Cited

U.S. PATENT DOCUMENTS

| | | | |
|---|---|---|---|
| 3,079,279 | * | 2/1963 | Van Loo, Jr. ............... 117/139.4 |
| 3,091,617 | * | 5/1963 | Burris ........................ 260/309.7 |
| 4,396,391 | * | 8/1983 | North ............................... 8/181 |

* cited by examiner

Primary Examiner—Joseph K. McKane
Assistant Examiner—Sonya N Wright
(74) Attorney, Agent, or Firm—Oblon, Spivak, McClelland, Maier & Neustadt, P.C.

(57) ABSTRACT

Described is a process for preparing mixtures of mixed-alkylated methylolated 4,5-dihydroxyimidazolidin-2-ones by reaction of methylolated 4,5-dihydroxyimidazolidin-2-one (DMDHEU) with a monohydric $C_{1-5}$ alcohol and a polyol selected from the group consisting of ethylene glycol, diethylene glycol, 1,2-propylene glycol, 1,3-propylene glycol, 1,2-butylene glycol, 1,3-butylene glycol, 1,4-butylene glycol, glycerol and polyethylene glycols of the formula $HO(CH_2CH_2O)_nH$ where $3 \leq n \leq 20$, the monohydric $C_{1-5}$ alcohol and the polyol each being used in an amount of from 0.1 to 2.0 mol equivalents, based on DMDHEU, and the reaction being carried out at temperatures from 20° C. to 70° C. and at a pH of from 1 to 2.5, and the pH being set to a value of from 4 to 8 after the reaction.

6 Claims, No Drawings

MIXTURES OF ALKYLATED METHYLOLATED 4,5-DIHYDROXY-IMIDAZOLIDIN-2-ONES

This application is a 371 of PCT/EP97/07318 filed Dec. 30, 1997.

The present invention relates to mixtures of mixed-alkylated methylolated 4,5-dihydroxyimidazolidin-2-ones. The invention also relates to a process for preparing the mixtures mentioned, to finishing baths thereof and to their use.

Methylolated 4,5-dihydroxyimidazolidin-2-ones are used in textile finishing as low-formaldehyde textile crosslinkers. They are also described as DMDHEU compounds (cf. Ullmann's Encyclopedia of Industrial Chemistry, Vol. A 26, pages 227 to 350]. These textile crosslinkers are effective for good crease recovery and reduced textile shrinkage. And DMDHEU derivatives reacted with methanol provide good easy-care effects. At the same time, the formaldehyde contents of the textiles treated with such DMDHEU derivatives are low. Yet there are disadvantages in the form of high emissions in use, i.e. in textile finishing, due to residual methanol or partly detached methanol.

U.S. Pat. No. 4,396,391 discloses the treatment of cellulosic textiles with polyol-derivatized DMDHEU. The DMDHEU reacted with polyols or their mixtures leads to low formaldehyde values in the treatment of textiles. However, the disadvantage of these hydroxyalkoxyalkylated DMDHEU derivatives is that their easy-care effects are inferior to methanol-derivatized DMDHEU compounds.

It is an object of the present invention to provide a low-formaldehyde textile crosslinker which provides good finishing effects with low formaldehyde values on the textile coupled with low emissions in textile finishing use. It shall impair the breaking strength of the fiber as little as possible, if at all, and confer good smoothness on it. In addition, it shall provide good easy-care effects.

This object is achieved by mixtures of mixed-alkylated methylolated 4,5-dihydroxyimidazolidin-2-ones, which are preparable by reaction of methylolated 4,5-dihydroxyimidazolidin-2-one (DMDHEU) with a monohydric $C_{1-5}$ alcohol and a polyol selected from the group consisting of ethylene glycol, diethylene glycol, 1,2-propylene glycol, 1,3-propylene glycol, 1,2-butylene glycol, 1,3-butylene glycol, 1,4-butylene glycol, glycerol and polyethylene glycols of the formula $HO(CH_2CH_2O)_nH$ where $3=n=20$, the monohydric $C_{1-5}$ alcohol and the polyol each being used in an amount of from 0.1 to 2.0 mol equivalents, based on DMDHEU, and the reaction being carried out at temperatures from 20° C. to 70° C. and at a pH of from 1 to 2.5, and the pH being set to a value of from 4 to 8 after the reaction.

The invention further provides a corresponding process for preparing these mixtures. The invention additionally provides an aqueous finishing bath for cellulosic textile materials, which comprises the said mixtures of the invention.

In the mixtures provided according to the invention, DMDHEU preferably has asymmetric substitution on the two nitrogen atoms of the imidazolidine ring. It is preferred for one of the two methylol groups of DMDHEU to be etherified with a methyl radical and the other methylol group to be derivatized by reaction with a polyol selected from the group consisting of ethylene glycol, diethylene glycol, 1,2-propylene glycol, 1,3-propylene glycol, 1,2-butylene glycol, 1,3-butylene glycol, 1,4-butylene glycol, glycerol and polyethylene glycols of the formula $HO(CH_2CH_2O)_nH$ where $3 \leq n \leq 20$, preferably diethylene glycol.

The mixtures of such asymmetrically substituted DMDHEU derivatives and their aqueous solutions are useful in textile finishing as low-formaldehyde textile crosslinkers because they have very low formaldehyde values. At the same time, the emissions in textile finishing are likewise reduced. In addition, the strength of the cellulosic textile materials treated therewith is distinctly improved as well. Another aspect is that the Monsanto smoothness image shows improved values.

The novel process for preparing the mixtures has both a single-stage and a two-stage variant. In the two-stage variant, an aqueous solution of DMDHEU is initially reacted with a monohydric $C_1$–$C_5$–alkohol, preferably methanol. From 0.1 to 2.0 mol equivalents of the alcohol are used. The pH during the reaction is within the range from 1 to 2.5. The temperature is from 20° C. to 70° C. The DMDHEU solution used has a solids content of typically 40–85% by weight. The reaction takes place in the presence of mineral acids, mixtures thereof or organic acids. Preferred acids are phosphoric acid or its mixtures with other mineral acids. The reaction times are within the range from 0.5 to 6 hours.

After this first reaction step, the aqueous solution is reacted in a second step with again from 0.1 to 2.0 mol equivalents of a polyol selected from the group consisting of ethylene glycol, diethylene glycol, 1,2-propylene glycol, 1,3-propylene glycol, 1,2-butylene glycol, 1,3-butylene glycol, 1,4-butylene glycol, glycerol and polyethylene glycols of the formula $HO(CH_2CH_2O)_nH$ where $3 \leq n \leq 20$. Preferably, the monohydric $C_{1-5}$ alcohol is used in an amount of from 0.7 to 2.0 mol equivalents and the polyol in an amount of from 0.8 to 1.4 mol equivalents, each based on DMDHEU. Preferably, the monohydric $C_{1-5}$ alcohol and the polyol are altogether used in an amount of from 1.7 to 2.9 mol equivalents, based on DMDHEU. The pH and the temperature of the reaction of the second step are within the ranges already mentioned in connection with the first step. Diethylene glycol is the preferred polyol. The order of the first process step and the second process step are advantageously changed. After the reaction has ended, the pH is adjusted to 4–8 by means of a customary base, for example sodium hydroxide or potassium hydroxide. The resulting solutions are adjusted to a desired solids content within the range from 40 to 85% by weight.

The novel mixtures can also be prepared in a single-stage process by reaction of aqueous solutions of DMDHEU with alcohol mixtures. Here alcohol mixtures are mixtures of the abovementioned alcohol components, namely of the monohydric $C_1$–$C_5$-alcohols and the polyols mentioned. The mixtures mentioned contain the monohydric $C_1$–$C_5$-alcohols and the polyols which are used according to the invention in ratios of 0.1–2.0:2.0–0.1 mol equivalents. The reaction takes place at a pH of from 1 to 2.5 and at from 20 to 70° C., preferably 20 to 50° C., in the presence of mineral acids, mixtures thereof or organic acids. The single-stage reaction is preferably carried out in the presence of phosphoric acid or its mixtures with other mineral acids. As with the two-stage reaction, the pH is adjusted to 4–8 by means of a customary base, for example sodium hydroxide or potassium hydroxide, after the reaction has ended. The preferred $C_1$–$C_5$-alcohol for the single-stage process is again methanol. And the preferred polyol is again diethylene glycol.

As already mentioned, the mixtures according to the invention are used for finishing cellulosic textile materials. Cellulosic textile materials are finished using a finishing bath which contains the mixtures according to the invention together with other, customary constituents, e.g. catalysts such as magnesium chloride, for example.

The Examples which follow illustrate the invention.

PREPARATION EXAMPLES

Inventive Example 1

To 116 parts of an aqueous methylolated 4,5-dihydroxyimidazolidin-2-one solution having a solids content of 70% by weight were added 16 parts of methanol. The pH was adjusted to a value within the range from 1.3 to 2.4 using 5 parts of phosphoric acid, and the alkylation was then carried out at 50° C. for 1.5 h. 58 parts of diethylene glycol were then added, and the second alkylation stage was carried out at 50° C. After about 1.5 h the reaction solution was cooled down and adjusted to pH 5 and to a solids content of 70% by weight.

Inventive Example 2

Inventive Example 1 was repeated, except that the order of the reactions with diethylene glycol and methanol was changed.

Inventive Example 3

To 239 parts of an aqueous methylolated 4,5-dihydroxyimidazolidin-2-one solution having a solids content of 68% by weight were added 127 parts of diethylene glycol. The pH was adjusted to a value within the range from 1.2 to 2.4 using a mixture of phosphoric acid and sulfuric acid, and the etherification was then carried out at 50° C. for 1 h. 26 parts of methanol were then added; the second etherification stage was carried out at 50° C. After about 1 h the reaction solution was cooled down and adjusted to pH 5 and a solids content of 69% by weight.

Inventive Example 4

To 130 parts of an aqueous methylolated 4,5-dihydroxyimidazolidin-2-one solution having a solids content of 75% by weight were added 83 parts of diethylene glycol. The pH was adjusted to a value within the range from 1.2 to 2.4 using phosphoric acid, and then the etherification was carried out at 50° C. for 1 h. Thereafter 10 parts of methanol were added, and the second etherification stage was carried out at 50° C. After about 1 h the reaction solution was cooled down and adjusted to a pH of 5 and a solids content of 71% by weight.

Inventive Example 5

To 178 parts of an aqueous methylolated 4,5-dihydroxyimidazolidin-2-one solution having a solids content of 74% by weight were added 49 parts of methanol and 59 parts of diethylene glycol. The pH was adjusted to a value within the range from 1.3 to 2.4 using phosphoric acid, and then the etherification was carried out at 50° C. for 2 h. After the reaction had ended, the mixture was cooled down and adjusted to pH 5 and to a solids content of 70% by weight.

Comparative Example 1

An etherified product prepared under standard conditions from aqueous methylolated 4,5-dihydroxyimidazolidin-2-one solution and methanol.

Comparative Example 2

A product alkylated from aqueous methylolated 4,5-dihydroxyimidazolidin-2-one solution and methanol under standard conditions and admixed with diethylene glycol.

Comparative Example 3

An etherified product prepared under standard conditions from aqueous methylolated 4,5-dihydroxyimidazolidin-2-one solution and diethylene glycol.

Application Testing a) Treatment of Test Fabrics

The products were used to prepare a 4% strength solution (based on 100% solids) additionally comprising 1.2% of magnesium chloride crystals as catalyst. The test fabric (cotton) was impregnated with these solutions in a pad-mangle to a wet pickup of 75%. It was then dried at 120° C. to a residual moisture content of 6–8%. Curing took place at 150° C. over 4 min.

b) Test Results

| Example | LAW 112 ppm | Monsanto rating md | Breaking loss in % | Emission factor g of C/kg of product** |
|---|---|---|---|---|
| Inventive 4 | 48 | 3 | 19 | 2 |
| Inventive 3 | 87 | 2.5 | 16 | 2 |
| Inventive 2 | 31 | 3 | 25 | 3 |
| Inventive 1 | 36 | 2.8 | 22 | 4 |
| Comparative 1 | 73 | 3.3 | 33 | 15 |
| Comparative 2 | 46 | 3 | 28 | 11 |
| Comparative 3 | 48 | 2 | 20 | 1 |

\* compared with untreated cotton
\*\* measured by FID method

We claim:

1. A process for preparing a mixture of mixed-alkylated methylolated 4,5-dihydroxyimidazolidin-2-ones, comprising:

reacting methylolated 4,5-dihydroxyimidazolidin-2-one (DMDHEU) with a monohydric $C_{1-5}$ alcohol and a polyol selected from the group consisting of ethylene glycol, diethylene glycol, 1,2-propylene glycol, 1,3-propylene glycol, 1,2-butylene glycol, 1,3-butylene glycol, 1,4-butylene glycol, glycerol, and polyethylene glycols of the formula $HO(CH_2CH_2O)_nH$, wherein $3 \leq n \leq 20$, wherein the monohydric $C_{1-5}$ alcohol and the polyol are each used in an amount of from 0.1 to 2.0 mol equivalents, based on the DMDHEU, and the reaction is conducted at a temperature from 20° to 70° C. and at a pH of from 1 to 2.5, followed by setting the pH to a value of from 4 to 8 after the reaction, wherein said mixture contains mixed-alkylated DMDHEUs which are asymmetrically substituted on the two nitrogen atoms of the imidazoline ring of the DMDHEU.

2. A process as claimed in claim 1, wherein said reacting is conducted in one or two stages.

3. A process as claimed in claim 1, wherein the monohydric $C_1$–$C_5$-alcohol is methanol and the polyol is diethylene glycol.

4. A process as claimed in claim 1, wherein said reacting is conducted at a temperature from 20 to 50° C.

5. A process as claimed in claim 1, wherein the monohydric $C_1$–$C_5$-alcohol is used in an amount of from 0.7 to 2.0 mol equivalents and the polyol is used in an amount of from 0.8 to 1.4 mol equivalents, based on the DMDHEU.

6. A process as claimed in claim 1, wherein the total amount of the monohydric $C_{1-5}$ alcohol and the polyol used is from 1.7 to 2.9 mol equivalents, based on DMDHEU.

\* \* \* \* \*